United States Patent
Li et al.

(10) Patent No.: US 11,186,552 B2
(45) Date of Patent: Nov. 30, 2021

(54) TEBUCONAZOLE POLYMORPH AND PREPARATION METHOD THEREFOR

(71) Applicant: East China University of Science and Technology, Shanghai (CN)

(72) Inventors: Zhong Li, Shanghai (CN); Guobin Ren, Shanghai (CN); Xiaoyong Xu, Shanghai (CN); Minghui Qi, Shanghai (CN); Jian Hu, Shanghai (CN); Chengyu Gong, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 16/764,698

(22) PCT Filed: Oct. 10, 2018

(86) PCT No.: PCT/CN2018/109675
§ 371 (c)(1),
(2) Date: May 18, 2020

(87) PCT Pub. No.: WO2019/095891
PCT Pub. Date: May 23, 2019

(65) Prior Publication Data
US 2021/0087152 A1    Mar. 25, 2021

(30) Foreign Application Priority Data

Nov. 17, 2017   (CN) .......................... 201711147036.2

(51) Int. Cl.
*C07D 249/08*    (2006.01)
*A01N 43/653*    (2006.01)

(52) U.S. Cl.
CPC ......... *C07D 249/08* (2013.01); *A01N 43/653* (2013.01); *C07B 2200/13* (2013.01)

(58) Field of Classification Search
CPC .................................................. C07D 249/08
See application file for complete search history.

(56) References Cited

FOREIGN PATENT DOCUMENTS

| CN | 101130522 A | 2/2008 |
|----|-------------|--------|
| CN | 102432556 A | 5/2012 |
| CN | 107176929 A | 9/2017 |
| DE | 3733755 A1 | 4/1989 |

OTHER PUBLICATIONS

Gregory, et al. Document No. 154:532501, retrieved from STN; entered in STN on May 13, 2001.*
Int'l Search Report dated Jan. 16, 2019 in Int'l Application No. PCT/CN2018/109675.

* cited by examiner

*Primary Examiner* — Shawquia Jackson
(74) *Attorney, Agent, or Firm* — Panitch Schwarze Belisario & Nadel LLP

(57) ABSTRACT

A tebuconazole polymorph and a preparation method therefor are described. In particular, a polymorph of (RS)-1-(4-chloropheny)-4,4-dimethyl-3-(1H-1,2,4-triazol-1-ylmethyl) pentan-3-ol, a preparation method therefor and use thereof are provided. The tebuconazole polymorph has a high purity and excellent crystallization properties, is stable under high humidity, high temperature and light conditions, has excellent solubility, and has high processing properties for formulations, high biological activities and good sterilization effects. The preparation method is simple, has stable processes, and can be implemented on a large scale. The polymorph can greatly improve the quality control and industrial application of tebuconazole-containing pesticides.

11 Claims, 4 Drawing Sheets

TEBUCONAZOLE POLYMORPH AND PREPARATION METHOD THEREFOR

CROSS-REFERENCE TO RELATED APPLICATIONS

This application is a Section 371 of International Application No. PCT/CN2018/109675, filed Oct. 10, 2018, which was published in the Chinese language on May 23, 2019 under International Publication No. WO 2019/095891 A1, which claims priority under 35 U.S.C. § 119(b) to Chinese Application No. 201711147036.2, filed on Nov. 17, 2017, the disclosures of which are incorporated herein by reference in their entireties.

TECHNICAL FIELD

The invention belongs to the field of medicinal chemistry, and specifically relates to the polymorph of tebuconazole and its preparation method.

BACKGROUND ART

Tebuconazole (a compound of formula I), i.e.

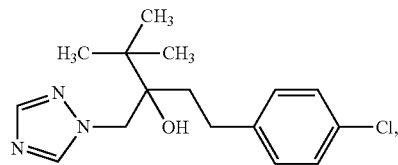

has a chemical name of (RS)-1-(4-chlorophenyl)-4,4-dimethyl-3-(1H-1, 2,4-triazol-1-ylmethyl) pentan-3-ol. The compound is a highly effective systemic fungicide used for seed treatment or leaf surface spraying of important economic crops. It can effectively prevent and control various rust disease, powdery mildew, net blotch, root rot, head blight, smut and seed-borne pestalotia theae of cereal crops. It can also be used to prevent and control *Cercospora arachidicola* and pestalotia theae, *Exobasidium vexans* Massee of tea tree, banana leaf spot disease, grape gray mold, powdery mildew, and so on.

The same compound having different crystal forms may have different solubilities and biological activities. In addition, the stabilities, fluidities and compressibilities may also be different. And these physical and chemical properties will have a certain effect on the application of the compound. According to the preparation method in the original compound patent DE 3733755, the prepared crystal form is named as crystal form 1, which has a low solubility.

Therefore, there is an urgent need in the art to develop polymorphs of the compound of formula I, which requires simple preparation methods, have good stability under high temperature, high humidity and light conditions, low hygroscopicity, high solubility, and can be large-scale produced.

SUMMARY OF THE INVENTION

The object of the present invention is to provide a polymorph of tebuconazole and its preparation method.

Another object of the present invention is to provide a polymorph of tebuconazole which has good stability under high temperature, high humidity and light conditions, high solubility and simple preparation method.

In a first aspect of the present invention, it provides a crystal of the compound of formula I,

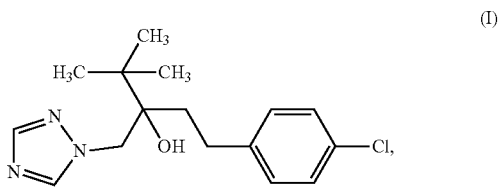

wherein, the crystal is crystal form 2, the X-ray powder diffraction pattern of which includes 3 or more 2θ values selected from the group consisting of 17.1±0.2°, 17.4±0.2°, 20.7±0.2°, 24.3±0.2°, 26.7±0.2°, and 27.5±0.2°.

In another preferred embodiment, the X-ray powder diffraction pattern of the crystal form 2 includes 3 or more 2θ values selected from the group consisting of 16.1±0.2°, 19.9±0.2°, 23.7±0.2°, 25.1±0.2°, 26.2±0.2°, 31.6±0.2°, and 37.3±±0.2°.

In another preferred embodiment, the X-ray powder diffraction pattern of the crystal form 2 further includes 3 or more 2θ values selected from the group consisting of 10.38±0.2°, 12.18±0.2°, 12.40±0.2°, 13.42±0.2°, 13.84±0.2°, 15.70±0.2°, 18.12±0.2°, 18.69±0.2°, 21.04±0.2°, 21.50±0.2°, 21.88±0.2°, 23.14±0.20, 24.60±0.20, 29.52±0.20, 29.84±0.20, 31.38±0.20, 32.40±0.20, 33.20±0.2°, 33.58±0.2°, 33.86±0.2°, 34.56±0.2°, 35.22±0.2°, 37.28±0.2°, 37.64±0.2°, 38.06±0.2°, 38.36±0.2°, 39.10±0.2°, 39.36±0.2°, 39.84±0.2°, 40.36±0.2°, 41.02±0.2°, 42±0.2°, 42.32±0.2°, 42.84±0.2°, 43.44±0.2°, and 44.12±0.2°.

In another preferred embodiment, the crystal form 2 has a 2θ (°) value selected from Table 1.

In another preferred embodiment, the X-ray powder diffraction pattern of the crystal form 2 is substantially characterized as shown in FIG. 1.

In another preferred embodiment, the TGA diagram of the crystal form 2 is substantially characterized as shown in FIG. 3.

In another preferred embodiment, the DSC pattern of the crystal form 2 has an endothermic peak in the range of 94.9-112.2° C.

In another preferred embodiment, the DSC pattern of the crystal form 2 is substantially characterized as shown in FIG. 2.

In another preferred embodiment, the purity of the crystal form 2 is greater than 95%, preferably, greater than 97%, more preferably, greater than 99%, and most preferably, greater than 99.5%.

In a second aspect of the present invention, it provides a pesticide composition, which comprises:

(a) the crystal according to the first aspect of the present invention, and (b) a pesticide-acceptable carrier.

In another preferred embodiment, the composition further comprises: an adjuvant, a wetting agent, a dispersant, an auxiliary dispersant, a synergist, a defoamer, or a combination thereof.

In another preferred embodiment, the composition comprises:

(a) 40-60 wt % of tebuconazole crystal form 2:
(b) 1-2 wt % of the wetting agent;
(c) 1-8 wt % of the dispersant;

(d) 3-7 wt % of the auxiliary dispersant;
(e) 0.5-2 wt % of the synergist;
(f) 0.1-0.5 wt % of the defoamer;
(g) a carrier (such as water);
based on the total weight of the composition.

In a third aspect of the present invention, it provides a method for preparing the crystal according to the first aspect of the present invention, which comprises the steps of:

(a) providing a solution of the compound of formula I in a first solvent; and (b) crystallizing above solution to form the crystal according to the first aspect of the present invention, which is crystal form 2.

In another preferred embodiment, in step (a), the compound of formula I is selected from the group consisting of amorphous compound, crystal form 1, crystal form 2, and a combination thereof.

In another preferred embodiment, after step (a), the method further includes: (a1) adding activated carbon to the solution.

In another preferred embodiment, the activated carbon is granular or powdery, preferably granular.

In another preferred embodiment, the first solvent in step (a) is selected from the group consisting of methylcyclohexane, methyl tert-butyl ether, methylcyclopentyl ether, and a combination thereof.

In another preferred embodiment, the first solvent in step (a) is an organic solvent B1 selected from the group consisting of methyl tert-butyl ether, methyl cyclopentyl ether, and a combination thereof.

In another preferred embodiment, the crystallization treatment in step (b) is (solvent) volatilization or vapor diffusion.

In another preferred embodiment, the crystallization treatment in step (b) is to place the solution in a solvent atmosphere of methylcyclohexane or n-heptane for vapor diffusion; preferably, the vapor diffusion solvent atmosphere further comprises solvent liquids in addition to the solvent gas.

In another preferred embodiment, the weight-volume ratio of the compound of formula I to the organic solvent B1 is 30 mg:(0.5-1.5) mL, preferably 30 mg:(0.8-1.2) mL.

In another preferred embodiment, the temperature at which the solvent is volatilized in step (b) is 10-30° C., preferably 15-25° C., and more preferably 18-22° C.

In another preferred embodiment, the temperature for the vapor phase diffusion is 10-35° C., preferably 20° C.-25° C.

In another preferred embodiment, the crystallization treatment in step (b) is cooling.

In another preferred embodiment, in the step (b), the solution is cooled to 5-25° C., preferably 10-20° C., more preferably 12-18° C.

In another preferred embodiment, the cooling rate is 1-5 min/° C., preferably 2-4 min/° C., more preferably 3 min/° C.

In another preferred embodiment, the step (b) comprises: cooling the solution for the first time, followed by warming, and cooling for the second time.

In another preferred embodiment, the first cooling is to cool to 55-65° C., preferably 58-62° C., more preferably 59-61° C.

In another preferred embodiment, the second cooling is to cool to 5-25° C., preferably 10-20° C., more preferably 12-18° C.

In another preferred embodiment, the warming is to warm to 65-75° C., preferably 68-72° C., more preferably 69-71° C.

In another preferred embodiment, the crystallization treatment in step (b) comprises: mixing the solution in step (a) with a second solvent, wherein the second solvent is an anti-solvent.

In another preferred embodiment, the first solvent is the organic solvent B1, and/or the second solvent is n-heptane or methylcyclohexane.

In another preferred embodiment, the amount ratio of the first solvent to the second solvent is 1:2-10, preferably 1:3-8, more preferably 1:4-6.

In another preferred embodiment, after step (b), the method further comprises: (c) separating the crystal form 2 from the solution in the previous step.

In another preferred embodiment, after step (b), the method further comprises: (d) drying the separated crystal form 2.

In a fourth aspect of the present invention, it provides a use of the crystal according to the first aspect of the present invention or the pesticide composition according to the second aspect of the present invention, for preventing or controlling diseases or for inhibiting harmful microorganisms in agriculture, forestry or horticulture.

In another preferred embodiment, the disease is a plant disease selected from the group consisting of rust disease, powdery mildew, net blotch, root rot, head blight, smut, *Cercospora arachidicola*, pestalotia theae, grape gray mold, *Exobasidium vexans* Massee of tea tree, banana leaf spot disease, and a combination thereof.

In another preferred embodiment, the harmful microorganisms are selected from the group consisting of *Ascomycetes, Basidiomycetes, Deuteromycetes, Oomycetes*, and a combination thereof.

In another preferred embodiment, the prevention or control is to prevent or control harmful microorganisms in agriculture, forestry or horticulture.

In another preferred embodiment, the administering method of the crystal or the pesticide composition is seed treatment or leaf surface spraying.

It should be understood that in the present invention, any of the technical features specifically described above and below (such as in the Examples) can be combined with each other, which will not redundantly be described one by one herein.

DETAILED DESCRIPTION OF THE INVENTION

Figure 1:
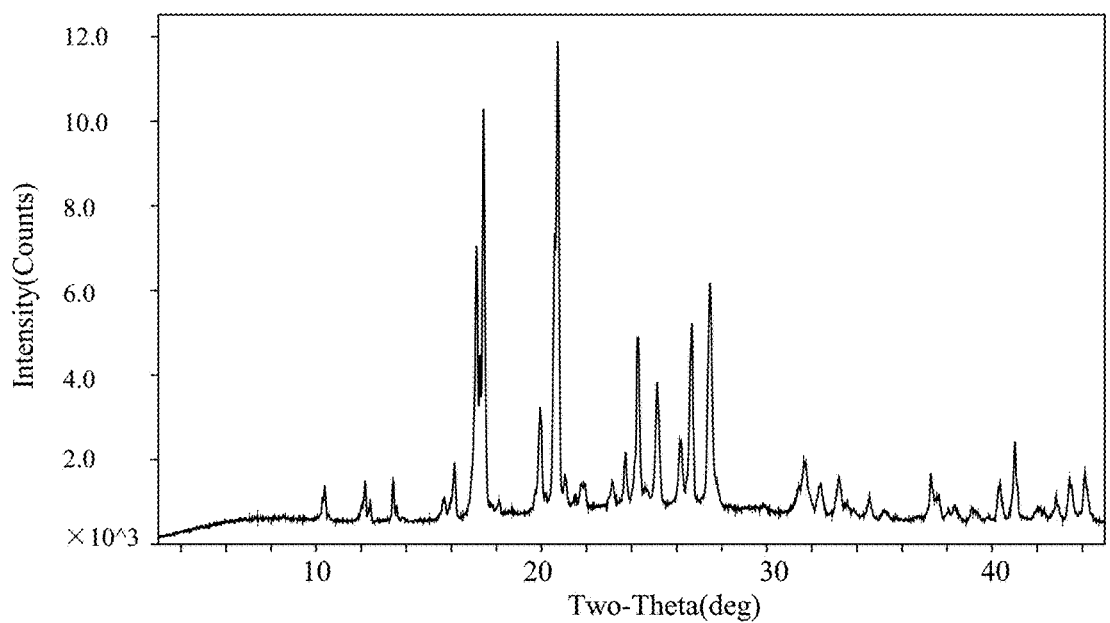
FIG. 1 shows the XRPD pattern of tebuconazole crystal form 2.

Through extensive and intensive research, the inventors unexpectedly discovered a polymorph of tebuconazole, its use and preparation method for the first time. The polymorph has a high purity, with good light and thermal stability and non-hygroscopicity, and is superior to the existing tebuconazole in terms of solubility, formulation processing performance and biological activity. It is suitable for the preparation of pesticide compositions that inhibit harmful microorganisms, so as to better prevent most diseases such as rust disease, powdery mildew, net blotch, root rot, head blight, smut, *Cercospora arachidicola*, pestalotia theae, grape gray mold, *Exobasidium vexans* Massee of tea tree, and banana leaf spot disease. In addition, the preparation method of the polymorph of the present invention is simple and suitable for large-scale industrial production. On this basis, the inventors have completed the present invention.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all values between 99 and 101 (e.g., 99.1, 99.2, 99.3, 99.4, etc.).

As used herein, the terms "contains" or "includes (comprises)" may be open ended, semi-close ended or close ended. In other words, the terms also include the meaning of "consisting essentially of" or "consisting of".

As used herein, the term "n or more 2θ values selected from the group consisting of" means including n and any positive integer greater than n (e.g. n, n+1, . . . ), wherein the upper limit Nup is the number of all 2θ peaks in the group. For example, "3 or more" includes not only each positive integer of 3, 4, 5, 6, 7, 8, 9, 10, 11, 12, 13, 14, 15, 16, 17, 18, 19, 20, 21, . . . and the upper limit Nup, but also "4 or more", "5 or more", "6 or more" and other ranges.

Compound of formula I

Tebuconazole (a compound of formula I), i.e.

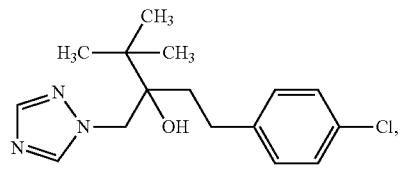

(I)

has a chemical name of (RS)-1-(4-chlorophenyl)-4,4-dimethyl-3-(1H-1, 2,4-triazol-1-ylmethyl) pentan-3-ol. The compound is a highly effective systemic fungicide used for seed treatment or leaf surface spraying of important economic crops. It can effectively prevent and control various rust disease, powdery mildew, net blotch, root rot, head blight, smut and seed-borne pestalotia theae of cereal crops. It can also be used to prevent and control *Cercospora arachidicola* and pestalotia theae, *Exobasidium vexans* Massee of tea tree, banana leaf spot disease, grape gray mold, powdery mildew, and so on.

Polymorph

Solids exist either in amorphous form or in crystal form. In the case of crystal forms, the molecules are localized within the three-dimensional lattice site. When a compound crystallizes out of a solution or slurry, it can crystallize in different spatial lattices (this property is called as "polymorphism") to form crystals with different crystal forms, which are called as "polymorph". Different polymorphs of a given substance may differ from each other in one or more physical properties such as solubility and dissolution rate, true specific gravity, crystal form, packing pattern, fluidity, and/or solid stability.

The polymorphic form of a compound can exhibit different melting points, hygroscopicity, stability, solubility, bioavailability, bioactivity and fluidity, etc., and these are important factors that affect the druggability.

As used herein, "crystal", "crystal of the present invention" or "polymorph" can be used interchangeably and refers to the crystal described in the first aspect of the present invention, and its crystal form is crystal form 2.

Crystallization

The solution can be manipulated so that the solubility limit of the compound of interest is exceeded, thereby completing crystallization on a production scale. This can be done in a number of ways, for example by dissolving the compound at a relatively high temperature and then cooling the solution to the temperature below the saturation limit. Or reducing the volume of the liquid by boiling, atmospheric evaporation, vacuum drying, or some other methods. The solubility of a compound of interest can be reduced by adding an anti-solvent or a solvent in which the compound has a low solubility or a mixture of such solvents. Another option is to adjust the pH to reduce solubility. For a detailed description of crystallization, see Crystallization, Third Edition, J W Mullens, Butterworth-Heineman Ltd., 1993, ISBN0750611294.

If it is desired that the salt formation and crystallization occur at the same time, and if the salt is less soluble in the reaction medium than the starting material, the addition of a suitable acid or base can result in direct crystallization of the desired salt. Also, in a medium where the final desired form is less soluble than the reactants, the completion of the synthetic reaction allows the final product to crystallize directly.

Optimization of the crystallization may include seeding the crystals in the desired form as crystal seed in the crystallization medium. In addition, many crystallization methods use a combination of the above strategies. One example is to dissolve the compound of interest in a solvent at high temperature, and then add an appropriate volume of anti-solvent in a controlled manner so that the system is just below the saturation level. At this point, crystal seed in the desired form can be added (and the integrity of the crystal seed is maintained) and the system is cooled to complete the crystallization.

In another preferred embodiment, the solvent is selected from the group consisting of methylcyclohexane, methyl tert-butyl ether, methylcyclopentyl ether, and a combination thereof.

Solvate

During the contact process between a compound or a drug molecule and a solvent molecule, there is an unavoidable situation that external and internal conditions cause the solvent molecule to form a eutectic with the compound molecule and remain in the solid substance. The substance formed after crystallization of the compound and the solvent is called a solvate. The types of solvents that easily form solvates with organic compounds are water, methanol, benzene, ethanol, ethers, aromatic hydrocarbons, heterocyclic aromatic hydrocarbons, and the like.

Hydrate is a special solvate. In the pharmaceutical industry, whether in the synthesis of raw materials, pharmaceutical preparations, drug storage, or evaluation of drug activity, hydrates have a separate discussion value because of their particularity.

In the present invention, the crystal of the compound of Formula I may be a non-solvate or a solvate.

Pesticide Composition

The "active ingredient" or "active compound" in the pesticide composition of the present invention refers to the compound of formula I described in the present invention, especially the compound of formula I existing in the crystal form of the present invention.

The "active ingredient" or "active compound" and the pesticide composition described in the present invention can be used for preventing or controlling diseases or for inhibiting harmful microorganisms in agriculture, forestry or horticulture.

Differential Scanning Calorimetry

Also known as "differential calorimetry scanning analysis" (DSC), it is a technique for measuring the relationship between the energy difference between the measured substance and the reference substance and the temperature during heating. The position, shape and number of peaks on the DSC spectrum are related to the nature of the substance, so they can be used to identify the substance qualitatively.

This method is commonly used in the art to detect various parameters such as the phase transition temperature, glass transition temperature, and reaction heat of a substance.

Preparation Method

In the preparation of tebuconazole crystal form 2, the method of temperature control crystallization, volatilization, elution or vapor diffusion is used. The method is simple and easy to implement, and is easy for industrial production.

Use

The present invention provides the use of tebuconazole crystal form 2 and its pesticide composition. The crystal form is highly efficient and broad-spectrum, and is a highly effective systemic fungicide for seed treatment or leaf surface spraying of important economic crops, which can effectively prevent and control various rust disease, powdery mildew, net blotch, root rot, head blight, smut, and seed-borne pestalotia theae of cereal crops. In addition, it can also be used to prevent and control *Cercospora arachidicola* and pestalotia theae, grape gray mold, powdery mildew, *Exobasidium vexans* Massee of tea tree, banana leaf spot disease, and so on with a good prevention and control effect.

The main advantages of the invention are:

(1) The crystal form 2 of the compound of formula I of the present invention has good thermal stability and non-hygroscopicity. It is stable under high temperature, high humidity and light conditions, and is superior to the present tebuconazole in terms of solubility, formulation processability and biological activity, and it has better disintegration performance.

(2) The preparation method of the crystal form 2 of the compound of formula I of the present invention is simple and suitable for large-scale industrial production.

(3) The crystal form 2 of the compound of formula I of the present invention can be used for preventing or controlling diseases or for inhibiting harmful microorganisms in agriculture, forestry or horticulture.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

The experimental materials and reagents used in the following examples can be obtained from commercial sources unless otherwise specified. Normal temperature or room temperature refers to 4° C.-25° C., preferably 15-25° C.

Test Methods:

XRD (X-ray powder diffraction) method: instrument model: Rigaku Ultima IV; target: Cu-Kα (40 kV, 40 mA); using a D/tex Ultra detector at room temperature. The scanning range is from 3° to 45 in the 2θ interval, and the scanning speed is 20°/minute.

Measurement differences related to the results of such X-ray powder diffraction analysis are generated by a variety of factors including: (a) error in sample preparation (e.g. sample height), (b) instrument error, (c) calibration difference, (d) operator errors (including errors that occur when determining the peak position), and (e) the nature of the substance (e.g. preferred orientation errors). Calibration errors and sample height errors often cause displacement of all peaks in the same direction. When a flat holder is used, a small difference in sample height will cause a large displacement of the XRPD peak position. Systematic studies have shown that a 1 mm difference in sample height can cause a peak shift of 20 up to 1°. These displacements can be identified from the X-ray diffraction pattern, and can be eliminated by compensating for the displacements (using system calibration factors for all peak position values) or recalibrating the instrument. As mentioned above, by applying system calibration factors to make peak positions consistent, measurement errors from different instruments can be corrected.

TGA (thermogravimetric analysis) method: instrument model: TA Q500 thermogravimetric analyzer; using $N_2$ atmosphere, with a heating rate of 10° C./min.

DSC (Differential Scanning Calorimetry) method: instrument model: TA Q2000; using $N_2$ atmosphere, with a heating rate of 10° C./min.

Example 1. Preparation of Crystal Form 1

The preparation of crystal form 1 refers to the preparation method in patent DE 3733755.

Example 2. Preparation of Crystal Form 2

2.1 100 g of raw material and 300 ml of methylcyclohexane were taken into a 500 ml crystallizer, heated to 80° C. and kept warm for 10 min until most of the solid were dissolved. 4 g activated carbon (particles) was added to remove impurities, stirred for 30 min. Filtered while hot, the filtrate was transferred to another 500 ml crystallizer, kept warm at 80° C. The temperature was cooled to 60° C., and kept for 30 minutes, and a large amount of crystals were precipitated. The temperature was warmed to 70° C. and kept for 4 hours. After the heat preservation, cooled to 15° C. at 3 min/° C., and kept for 10 min. Filtered with suction, collected and dried in a blast oven at 60° C.

2.2 Using the method of solvent volatilization, 30 mg of raw material and 1 mL of methyl tert-butyl ether were taken into a 10 mL transparent sample bottle, and volatilized at a room temperature of 20° C. After crystallizing, it was collected and dried in a vacuum oven at normal temperature.

2.3 Using gas-phase diffusion method, 30 mg of raw material and 1 mL of methyl tert-butyl ether or methylcyclopentyl ether were taken into a 10 mL transparent sample bottle, and then it was placed in a mL reagent bottle containing 30 mL of methylcyclohexane, sealed and stored. After crystallization, it was collected and dried in a vacuum oven at normal temperature.

2.4 Using the elution method, 30 mg of raw material and 1 mL of methyl tert-butylether were taken into a 10 mL transparent sample bottle. After dissolving, 5 mL of n-heptane was added, sealed for storage. After crystallization, it was collected and dried in a vacuum oven at normal temperature.

The XRD pattern of the obtained crystal form 2 is basically shown in FIG. 1, and the diffraction angle data is basically shown in Table 1 below, wherein the error range of 2θvalue is ±0.2.

TABLE 1

XRD data for crystal form 2

| 2θ | d (A) | I (relative intensity) % |
|---|---|---|
| 10.38 | 8.5148 | 7.6 |
| 12.18 | 7.2614 | 8.9 |
| 12.40 | 7.1312 | 4.2 |
| 13.42 | 6.5922 | 8.9 |
| 13.84 | 6.3936 | 0.9 |
| 15.70 | 5.6395 | 4.3 |
| 16.14 | 5.4868 | 11.8 |
| 17.12 | 5.175 | 58 |
| 17.42 | 5.0858 | 88.2 |
| 18.12 | 4.8914 | 2.1 |
| 18.69 | 4.7435 | 1 |
| 19.94 | 4.4489 | 20.9 |
| 20.72 | 4.2831 | 100 |
| 21.04 | 4.2182 | 6.1 |
| 21.50 | 4.1294 | 2.3 |
| 21.88 | 4.0584 | 4.9 |
| 23.14 | 3.8403 | 4.6 |
| 23.74 | 3.7454 | 10.2 |
| 24.26 | 3.6652 | 34.9 |
| 24.60 | 3.616 | 3 |
| 25.14 | 3.5393 | 25.4 |
| 26.20 | 3.3988 | 13.1 |
| 26.68 | 3.3388 | 38.6 |
| 27.48 | 3.2431 | 47.6 |
| 29.52 | 3.0231 | 0.9 |
| 29.84 | 2.9917 | 1.2 |
| 31.38 | 2.848 | 4.6 |
| 31.64 | 2.8253 | 11 |
| 32.40 | 2.7611 | 5.6 |
| 33.20 | 2.6961 | 8 |
| 33.58 | 2.6668 | 2.9 |
| 33.86 | 2.645 | 1.4 |
| 34.56 | 2.5932 | 4.4 |
| 35.22 | 2.5462 | 1.8 |
| 37.28 | 2.4098 | 9.8 |
| 37.64 | 2.3879 | 5.2 |
| 38.06 | 2.3622 | 2 |
| 38.36 | 2.3447 | 2.9 |
| 39.10 | 2.3018 | 2.8 |
| 39.36 | 2.2875 | 1.8 |
| 39.84 | 2.2607 | 0.7 |
| 40.36 | 2.233 | 7.5 |
| 41.02 | 2.1986 | 16.8 |
| 42 | 2.1494 | 2.3 |
| 42.32 | 2.1341 | 2.1 |
| 42.84 | 2.1092 | 4.9 |
| 43.44 | 2.0814 | 8.3 |
| 44.12 | 2.0509 | 10.5 |

Figure 2:
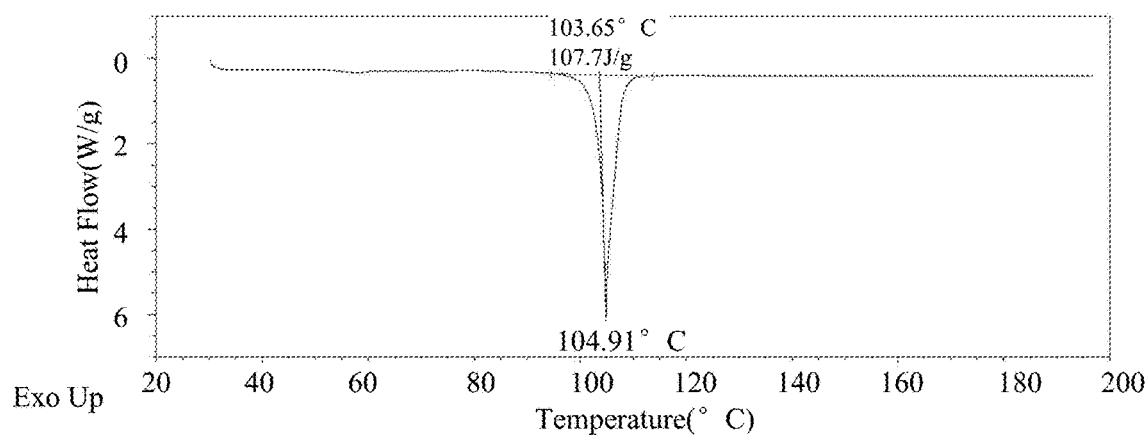
FIG. 2 shows the DSC pattern of tebuconazole crystal form 2.

The DSC pattern of crystal form 2 is basically shown in FIG. 2. The endothermic peak corresponds to the melting decomposition process and has an endothermic peak in the range of 94.9-112.2° C.

Figure 3:
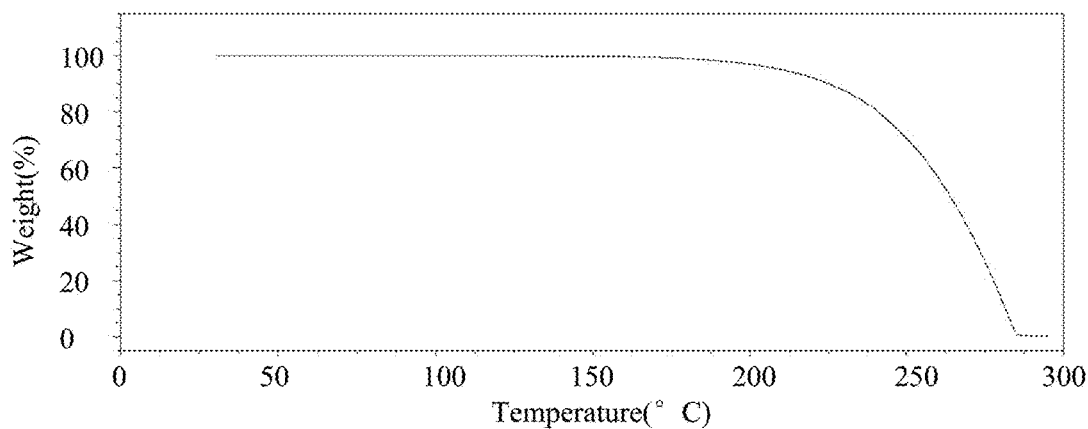
FIG. 3 shows the TGA graph of tebuconazole crystal form 2.

The TGA pattern of crystal form 2 is basically shown in FIG. 3, and there is almost no weight loss before decomposition.

Figure 4:
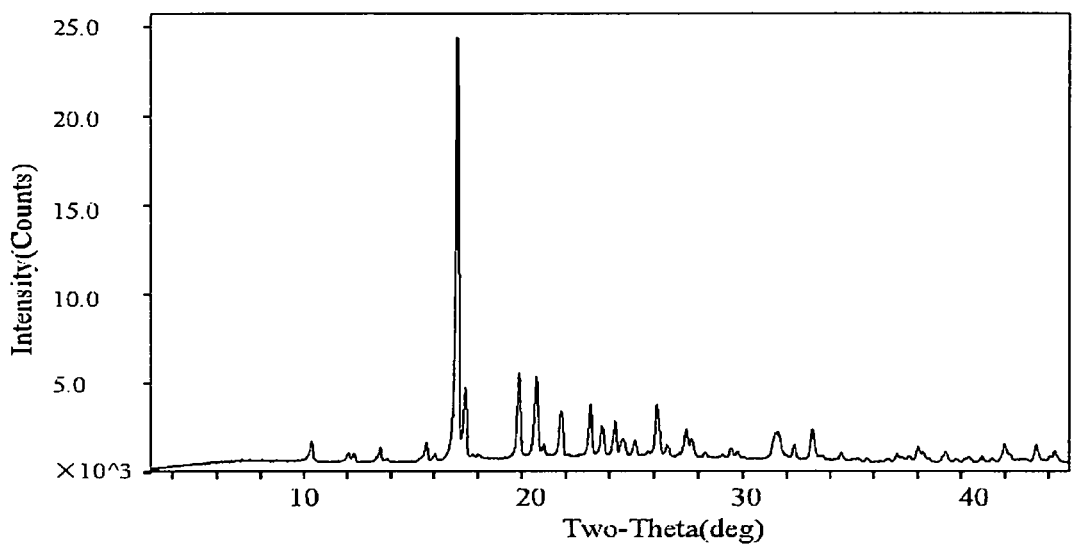
FIG. 4 shows the XRPD pattern of the crystal form 2 after high temperature stability for five days.
Figure 5:
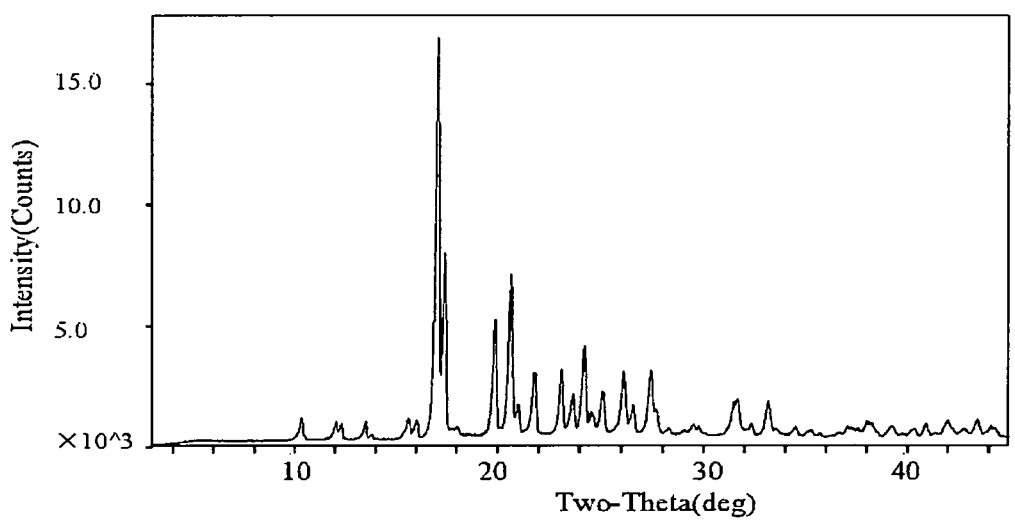
FIG. 5 shows the XRPD pattern of the crystal form 2 after high temperature stability for ten days.

Example 3. Investigation of the Stability of Crystal Form 2 Tebuconazole 3.1 High Temperature Stability The crystal form 2 tebuconazole sample in Example 2 was placed in an oven at 60±2° C. After 5 and 10 days, the sample was taken out for XRPD test to investigate the crystalline stability of the sample to temperature. As shown in FIG. 4 and FIG. 5, the results show that the crystal form 2 sample is stable under this condition.

3.2 High Humidity Stability

Figure 6:
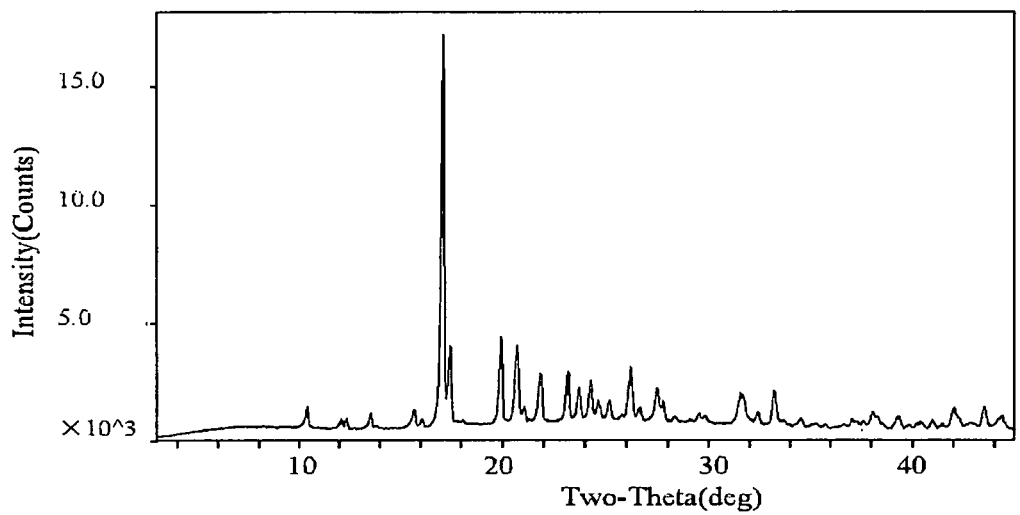
FIG. 6 shows the XRPD pattern of the crystal form 2 after high humidity stability for five days.
Figure 7:
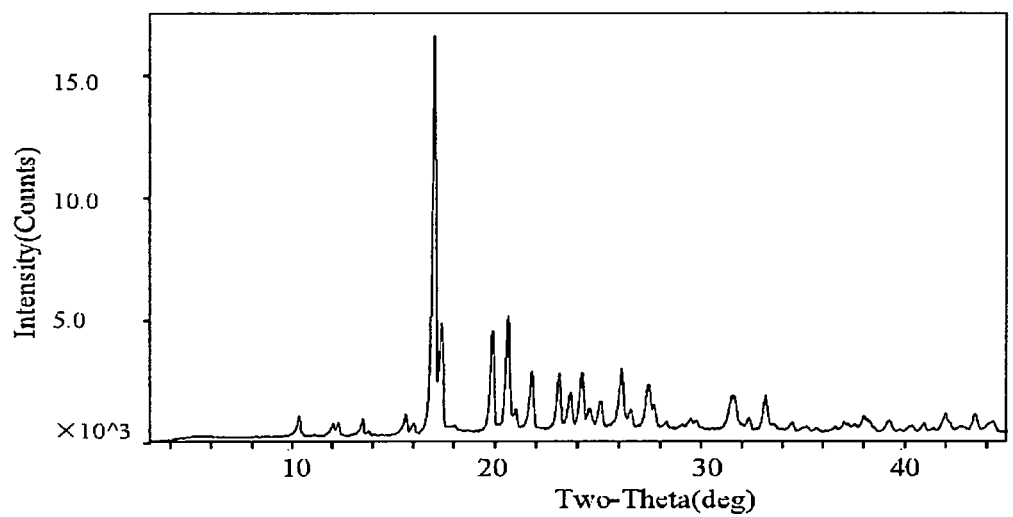
FIG. 7 shows the XRPD pattern of the crystal form 2 after high humidity stability for ten days.

The crystal form 2 tebuconazole sample in Example 2 was placed under 90±5% humidity conditions, and the samples were taken out for XRPD test after 5 days and 10 days to investigate the crystalline stability of the samples to humidity. As shown in FIG. 6 and FIG. 7, the results show that the crystal form 2 sample is stable under this condition.

3.3 Light Stability

Figure 8:
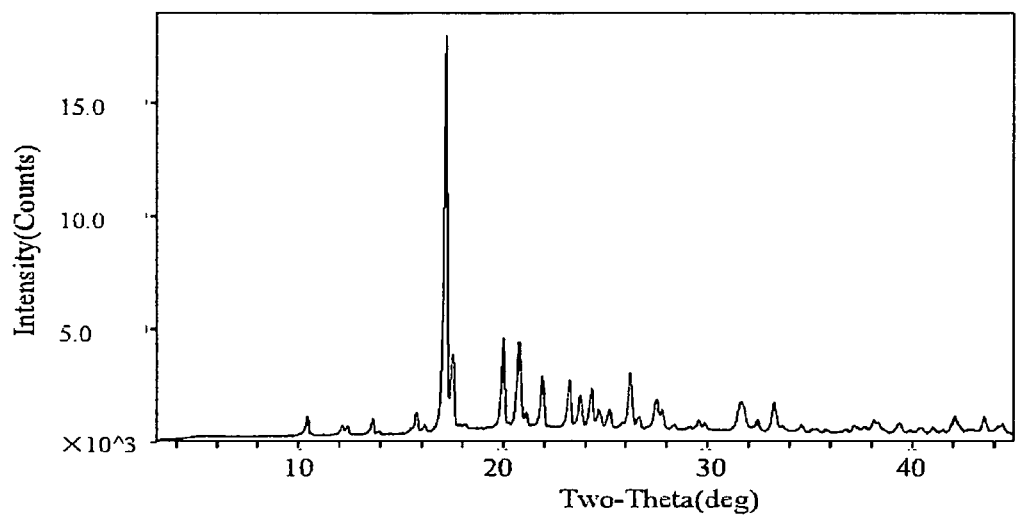
FIG. 8 shows the XRPD pattern of the crystal form 2 after light stability for five days.
Figure 9:
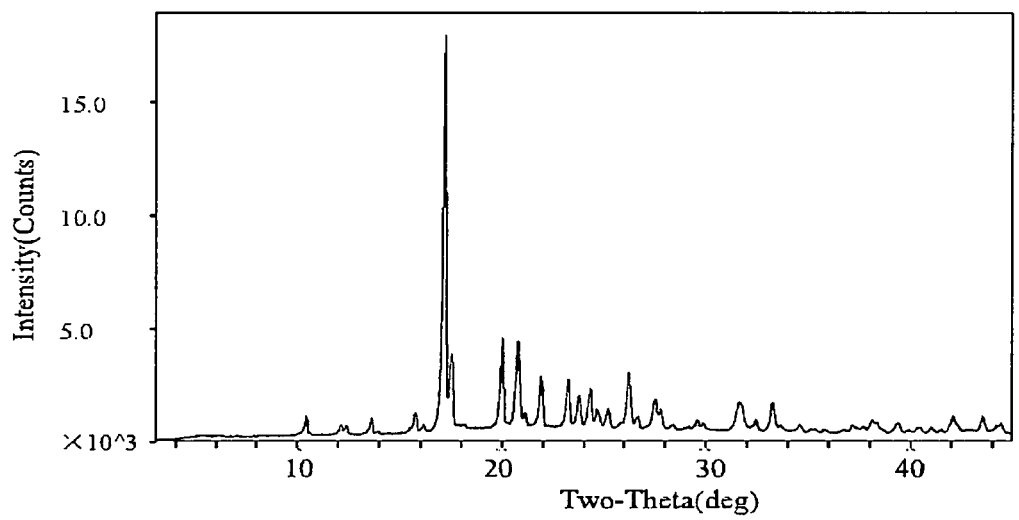
FIG. 9 shows the XRPD pattern of the crystal form 2 after light stability for ten days.

The crystal form 2 tebuconazole sample in Example 2 was placed under 4500±500 lux light intensity, and after 5 days and 10 days, the sample was taken out for XRPD test to investigate the crystal form stability of the sample to light. As shown in FIG. 8 and FIG. 9, the results show that the crystal form 2 sample is stable under this condition.

Example 4. Comparison of the Solubilities of Crystal Form 1 and Crystal Form 2

Excess crystal form 1 and crystal form 2 were weighed and suspended in ethanol, shaken for 12 h, and high performance liquid chromatography was used to test the solubility. The test results are shown in Table 2 below. It can be concluded that the solubility of crystal form 2 in ethanol is significantly greater than that of crystal form 1, that is, about 1.7 times of that of crystal 1.

TABLE 2

Solubilities of crystal form 2 and crystal form 1

| Crystal form | Solubility (g/L) |
|---|---|
| crystal form 1 | 92.1 |
| crystal form 2 | 156.2 |

Example 5. Comparison of the Processing Performances of the Water-Dispersible Granules Preparation of Crystal Form 1 and Crystal Form 2

The same quality of crystal form 1 and crystal form 2 were weighed respectively, added with adjuvants, and placed in a universal mill for processing. The test results are shown in Table 3 below. Crystal form 2 is easier to be processed into water-dispersible granules preparation and has better disintegration properties.

TABLE 3

Processing properties of water-dispersible granules preparation of crystal form 2 and crystal form 1

| | 50% Tebuconazole WDG | |
|---|---|---|
| lot number | Crystal form 1 | Crystal form 2 |
| Adjuvants | Feeding quality percentage % | |
| Tebuconazole | 50 | 50 |
| wetting agent | 1.5 | 1.5 |
| Dispersant 1 | 2 | 2 |
| Dispersant 2 | 4 | 4 |
| Auxiliary dispersant | 5 | 5 |
| Synergist | 1 | 1 |
| Defoamer | 0.3 | 0.3 |
| Carrier | Make up | Make up |
| Milling method | Universal mill | |
| Particle size μm  D50 | 10.8 | 11.94 |
| D90 | 60.4 | 22.99 |
| Added water content | 18 | 18 |
| Granulation process | The powder is not easy to crush. The appearance of the raw material is uneven filamentous crystals. The powder is difficult to wet. The powder is easy to disperse during kneading. The particles are not full, and after dried, they are fragile. Dead particles are produced during disintegration process. | The powder is easier to crush, and wetting is easier. The kneading process is relatively easy. The particles are full. There are no dead particles during disintegration process, and there is a trailing phenomenon. |
| Disintegrability (S) | Poor disintegration, 30s | Good disintegration, 15s |

Example 6. Comparison of the Biological Activities of the Water-Dispersible Granules Preparation of Crystal Form 1 and Crystal Form 2

The water-dispersible granules preparations with 50% of crystal form 1 and crystal form 2 were formulated into solutions, respectively, and the plants were protected by live spray. The test results are shown in Table 4 below. Crystal form 2 has better prevention and control effect.

TABLE 4

Comparison of the biological activities of crystal form 2 and crystal form 1

Test number: East China Institute of Technology 01
Test Type: ☐ General Screening ☐ Initial Screening ☐ Re-screening ■ In-depth Screening
Test purpose: wheat white powder
Test method: live spray protection
Test Date: 2017.11.13     Investigation Date: 2017.11.24

| | | Concentration (mg/L)/prevention and control effect (%) | | | |
|---|---|---|---|---|---|
| Bio-No. | No. | 10 | 2.5 | 0.625 | 0.15625 |
| 5 | crystal form 1 50% WDG | 70 | 0 | 0 | 0 |
| 6 | crystal form 2 50% WDG | 97 | 0 | 0 | 0 |
| 7 | 96% tebuconazole TC | 100 | 50 | 30 | 0 |

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A crystal of a compound of formula I,

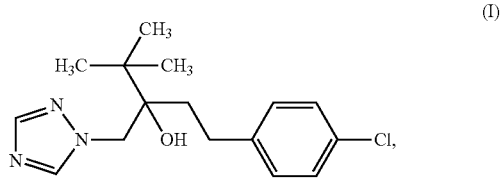

wherein, the crystal is crystal form 2, the X-ray powder diffraction pattern of which includes 3 or more 2θ values selected from the group consisting of 17.1±0.2°, 17.4±0.2°, 20.7±0.2°, 24.3±0.2°, 26.7±0.2°, and 27.5±0.2°.

2. The crystal according to claim 1, wherein the X-ray powder diffraction pattern of the crystal form 2 includes 3 or more 2θ values selected from the group consisting of 16.1±0.2°, 19.9±0.2°, 23.7±0.2°, 25.1±0.2°, 26.2±0.2°, 31.6±0.2°, and 37.3±0.2°.

3. The crystal according to claim 1, wherein the X-ray powder diffraction pattern of the crystal form 2 further includes 3 or more 2θ values selected from the group consisting of 10.38±0.2°, 12.18±0.2°, 12.40±0.2°, 13.42±0.2°, 13.84±0.2°, 15.70±0.2°, 18.12±0.2°, 18.69±0.2°, 21.04±0.2°, 21.50±0.2°, 21.88±0.2°, 23.14±0.2°, 24.60±0.2°, 29.52±0.2°, 29.84±0.2°, 31.38±0.2°, 32.40±0.2°, 33.20±0.2°, 33.58±0.2°, 33.86±0.2°, 34.56±0.2°, 35.22±0.2°, 37.64±0.2°, 38.06±0.2°, 38.36±0.2°, 39.10±0.2°, 39.36±0.2°, 39.84±0.2°, 40.36±0.2°, 41.02±0.2°, 42±0.2°, 42.32±0.2°, 42.84±0.2°, and 43.44±0.2°, 44.12±0.2°.

4. The crystal according to claim 1, wherein the X-ray powder diffraction pattern of the crystal form 2 is substantially characterized as shown in FIG. 1.

5. The crystal according to claim 1, wherein the TGA pattern of the crystal form 2 is substantially characterized as shown in FIG. 3.

6. The crystal according to claim 1, wherein the DSC pattern of the crystal form 2 has an endothermic peak in the range of 94.9-112.2° C.

7. The crystal according to claim 1, wherein the DSC pattern of the crystal form 2 is substantially characterized as shown in FIG. 2.

8. A pesticide composition, which comprises:
    (a) the crystal according to claim 1, and (b) a pesticide-acceptable carrier.

9. A method for preparing the crystal according to claim 1, which comprises the steps of:
    (a) providing a solution of the compound of formula I in a first solvent; and
    (b) crystallizing above solution to form the crystal according to claim 1, which is crystal form 2.

10. A method of preventing or controlling diseases or for inhibiting harmful microorganisms in agricultural, forestry, or horticulture using the crystal according to claim 1.

11. A method of preventing or controlling diseases or for inhibiting harmful microorganisms in agricultural, forestry, or horticulture using the pesticide composition according to claim 8.

* * * * *